United States Patent [19]

Kimura

[11] Patent Number: 4,641,242

[45] Date of Patent: Feb. 3, 1987

[54] RADIATION IMAGE RECORDING AND REPRODUCING SYSTEM

[75] Inventor: Tsutomu Kimura, Kanagawa, Japan

[73] Assignee: Fuji Photo Film Co., Ltd., Kanagawa, Japan

[21] Appl. No.: 587,717

[22] Filed: Mar. 8, 1984

[30] Foreign Application Priority Data

Mar. 11, 1983 [JP] Japan .................................. 58-40508

[51] Int. Cl.[4] .................................................. G01J 1/29

[52] U.S. Cl. ..................................... 364/414; 250/337; 382/6

[58] Field of Search ................ 364/414, 415; 250/337; 382/6

[56] References Cited

U.S. PATENT DOCUMENTS

| | | | |
|---|---|---|---|
| 4,160,906 | 7/1979 | Daniels et al. | 364/414 X |
| 4,276,473 | 6/1981 | Kato et al. | 250/337 X |
| 4,284,889 | 8/1981 | Kato et al. | 250/337 X |
| 4,315,318 | 2/1982 | Kato et al. | 364/414 X |

*Primary Examiner*—Jerry Smith
*Assistant Examiner*—Charles B. Meyer
*Attorney, Agent, or Firm*—Sughrue, Mion, Zinn, Macpeak & Seas

[57] ABSTRACT

A stimulable phosphor is exposed to a radiation passing through an object to have a radiation image stored therein, and then exposed to stimulating rays to read out the radiation image and obtain an electric image signal. The image signal is processed under conditions suitable for the type of image recording and used to reproduce a visible image. The conditions of exposure to the radiation and the image processing conditions are adjusted by a single action of selecting the setting conditions predetermined according to the type of image recording. Also, read-out of an identification code provided on the stimulable phosphor and the exposure of the radiation are started by a single action. Or, the read-out of the identification code is conducted in response to memorizing of information on the object.

6 Claims, 6 Drawing Figures

RADIATION IMAGE RECORDING AND REPRODUCING SYSTEM

BACKGROUND OF THE INVENTION

1. Field of the Invention

This invention relates to a radiation image recording and reproducing system. This invention particularly relates to a radiation image recording and reproducing system wherein a stimulable phosphor is exposed to a radiation passing through an object to have a radiation image stored therein, the stimulable phosphor is scanned with stimulating rays which cause it to emit light in proportion to the radiation energy stored, the emitted light is photoelectrically detected and converted to an electric image signal, the electric image signal is processed, and a visible image is reproduced by use of the processed electric image signal.

2. Description of the Prior Art

A radiation image recording and reproducing system using a stimulable phosphor is described, for example, in U.S. Pat. Nos. 4,258,264, 4,276,473 and 4,315,318, U.S. Patent Appln. Ser. No. 220,780, Japanese Unexamined Patent Publication No. 56(1981)-11395, and "Nikkan Kogyo Shinbun" (Daily Industrial Newspaper), Nov. 6, 1982 edition. The radiation image recording and reproducing system comprises the steps of (i) exposing the stimulable phosphor to a radiation such as X-rays passing through an object to have a radiation image stored therein, (ii) scanning the stimulable phosphor with stimulating rays which cause it to emit light in proportion to the radiation energy stored, (iii) photoelectrically detecting the emitted light and converting it into an electric image signal, and (iv) reproducing a visible image by use of the obtained electric image signal. In this system, image recording can be conducted by use of a radiation exposure dose markedly lower than in the conventional radiography using a silver halide photographic material. Further, by processing the electric image signal in various manners, it is possible to obtain a radiation image having a markedly improved image quality, particularly a high diagnostic efficiency and accuracy. Thus this system is very advantageous in practical use, particularly for medical diagnosis.

In order to put the above-mentioned radiation image recording and reproducing system into practice, many problems with regard to practical use must be solved. Thus a radiation diagnostic system useful for medical purposes can be realized only after the problems with regard to practical use are solved one by one. Particularly, when the radiation diagnostic system for medical purposes is used for diagnoses of many patients or many examination objects as in the case of mass medical examinations, the system must be such that the diagnoses of many patients or many examination objects can be carried out correctly at a high efficiency.

As described above, the aforesaid radiation image recording and reproducing system provides high diagnostic performance by appropriately processing the electric image signal obtained by photoelectrically reading out the radiation image stored in the stimulable phosphor. Therefore, image processings must be carried out appropriately according to the type of image recording. That is, most suitable image processing conditions should be selected according to factors such as the portion of the object to be image-recorded (the heart, the chest, or the like), the image recording method (plain image recording, contrasted image recording, subtraction image recording, or the like), and the diagnostic purpose (mass medical examination, close examination, or the like). The image processings embrace all possible image processings for improving the quality of radiation images according to the portion of the object, for example, contrast adjustments, density level adjustments, image gradation processings, frequency processings, and unsharp mask processings. The image processings also embrace image subtraction processings.

Further, in the aforesaid radiation image recording and reproducing system, exposure conditions of the radiation source, such as an X-ray source, should also preferably be adjusted as required with respect to the above-described type of image recording. Specifically, image recording should be conducted under the most suitable radiation exposure conditions by changing, for example, the tube voltage, the tube current, the exposure time, and the focusing point size of the radiation source.

As described above, in the aforesaid radiation image recording and reproducing system, it is desired that the radiation exposure conditions of the radiation source and the image processing conditions be adjusted to the most suitable conditions according to the aforesaid type of image recording. However, when the radiation image recording and reproducing system is continuously used for recording and reproducing radiation images of many patients or examination objects in mass medical examinations or the like, it is troublesome to adjust the radiation exposure conditions and the image processing conditions for each patient or each examination object every time image recording and reproducing are conducted. Also, in such a case, adjustment errors or operation errors readily arise.

Also, when the aforesaid radiation image recording and reproducing system is put into practice, it is of course necessary to record or memorize information on the patients or the examination objects, for example, the sex, the names, the date of image recording, and the portion of the object, in relation to the image information recorded. In practice, the stimulable phosphor used for recording image information in the aforesaid radiation image recording and reproducing system is fabricated into a sheet-like shape, and the stimulable phosphor sheets are provided with identification codes such as bar codes for identifying the stimulable phosphor sheets. Accordingly, the identification codes of the stimulable phosphor sheets are memorized in relation to the aforesaid object information, and used to clarify the relationship between the image information recorded in the stimulable phosphor sheets and the object information at the time of image recording and reproducing. The operations for correctly clarifying the relationship between the object information and the identification codes and for memorizing the object information and the identification codes in relation to each other are not always possible to conduct when a large number of objects have to be handled. Thus there is a risk of mistakes arising in such operations. However, the aforesaid operation must be carried out without fail for all objects. This problem must also be solved in practical use of the radiation image recording and reproducing system.

SUMMARY OF THE INVENTION

The primary object of the present invention is to provide a radiation image recording and reproducing system free of operation error and exhibiting a high efficiency, wherein adjustment of the radiation exposure conditions for image recording and adjustment of the image processing conditions at the time of image processing are carried out by a single operation.

Another object of the present invention is to provide a radiation image recording and reproducing system wherein operation errors are eliminated and the efficiency is improved by conducting the adjustment of the radiation exposure conditions, the adjustment of the image processing conditions, and read-out of an identification code of a stimulable phosphor by a single operation.

The specific object of the present invention is to provide a radiation image recording and reproducing system wherein the adjustment of the radiation exposure conditions and the adjustment of the image processing conditions are carried out by a single operation, and read-out of the identification code of the stimulable phosphor is conducted automatically in response to an operation for memorizing the object information.

The radiation image recording and reproducing system in accordance with the present invention comprises simultaneously adjusting the radiation exposure conditions and the image processing conditions by a single action for selecting preset conditions predetermined according to the type of image recording.

In another aspect of the present invention, the adjustment of the radiation exposure conditions, the adjustment of the image processing conditions, and read-out of an identification code of a stimulable phosphor are conducted by the same operation, thereby improving the efficiency and preventing operation errors.

In a further aspect of the present invention, the radiation exposure conditions and the image processing conditions are simultaneously adjusted as described above, and read-out of the identification code of the stimulable phosphor is automatically conducted in response to an operation for memorizing the object information. In this aspect, the read-out of the identifiction code and memorizing of the object information are carried out simultaneously, thereby preventing operation errors.

In the present invention, the radiation exposure conditions and the image processing conditions which should be determined for respective objects are simultaneously adjusted by a single operation. Thus, since two adjustment operations can be achieved by a single operation, the radiation image recording and reproducing system of the present invention exhibits a high efficiency and is free of operation errors. This is very advantageous in practical use.

By "single operation" is meant the series of actions conducted by the operator (radiologist) as the selecting operation according to the type of image recording, for example, the series of actions of selecting and depressing the keys on a keyboard which specify the portion of the object (the abdomen, the frontal chest, or the like), and/or the image recording method (plain image recording, angiography, or the like), and/or the purpose of image recording. Even when two or more keys (e.g. a "frontal chest" key, a "plain image recording" key, and a "setting" key) are depressed, the operation of depressing these keys is called a single operation insofar as the depressing of these keys is a series of interrelated actions which have to be conducted for one type of image recording.

As described above, in another aspect of the present invention, read-out of an identification code of a stimulable phosphor is conducted by the same action as that for the adjustment of the radiation exposure conditions and the adjustment of the image processing conditions. However, this does not necessarily mean that the read-out of the identification code and the adjustments of the aforesaid conditions are carried out exactly simultaneously. For example, the adjustments of the aforesaid conditions may first be conducted, and then the read-out of the identification code may be automatically carried out after several seconds insofar as the adjustments and the read-out are effected by a single operation (for example, by a series of actions of depressing the keys on the keyboard as described above). Also in such a case, the adjustments of the aforesaid conditions and the read-out of the identification code should be regarded as being conducted by a single operation since the time lag therebetween is not caused by a different manual operation, but instead is a mechanical delay or an electrical delay.

In a further aspect of the present invention, the read-out of the identificaation code of the stimulable phosphor is automatically conducted in response to an action of memorizing the object information. For example, when a magnetic card (patient identification card or patient ID card) issued for each patient and carrying data on the sex, the name and the birth date of the patient, or a patient ID number magnetically recorded therein is inserted into a magnetic card reader, the read-out of a bar code (identification code) of the stimulable phosphor may be started simultaneously with the start of the read-out of the magnetic card. Or, the read-out of the bar code of the stimulable phosphor may be started in response to the manual entry of the aforesaid object information from a keyboard or the like (i.e. in response to the memorizing action).

It is also possible to magnetically record the data on the portion of the object in the aforesaid patient ID card. For example, the data on the portion of the patient the radiation image of which should be recorded in the stimulable phosphor, such as the data specifying the abdomen, is magnetically recorded together with the data on the name of the patient or the like in the patient ID card. Thus, not only the read-out of the identification code but also the selection of the aforesaid radiation exposure conditions and image processing conditions according to the type of image recording can be achieved only by the action of inserting the patient ID card into the magnetic card reader. In this case, the adjustments of the radiation exposure conditions and the image processing conditions, the read-out of the identification code, and memorizing of the object information are carried out by a single operation.

In order to carry out the aforesaid items by a single operation, various other methods are possible by utilizing the action of selecting suitable radiation exposure conditions and image processing conditions from many predetermined conditions. (When the patient ID card is used and the data stored therein is read out by the magnetic card reader, the read-out signal is used for searching the corresponding conditions from those stored in a memory. This step can also be regarded as selection.) All of such possible methods are embraced in the scope of the present invention.

DESCRIPTION OF THE PREFERRED EMBODIMENTS

The present invention will hereinbelow be described in further detail with reference to the accompanying drawings.

Figure 1:
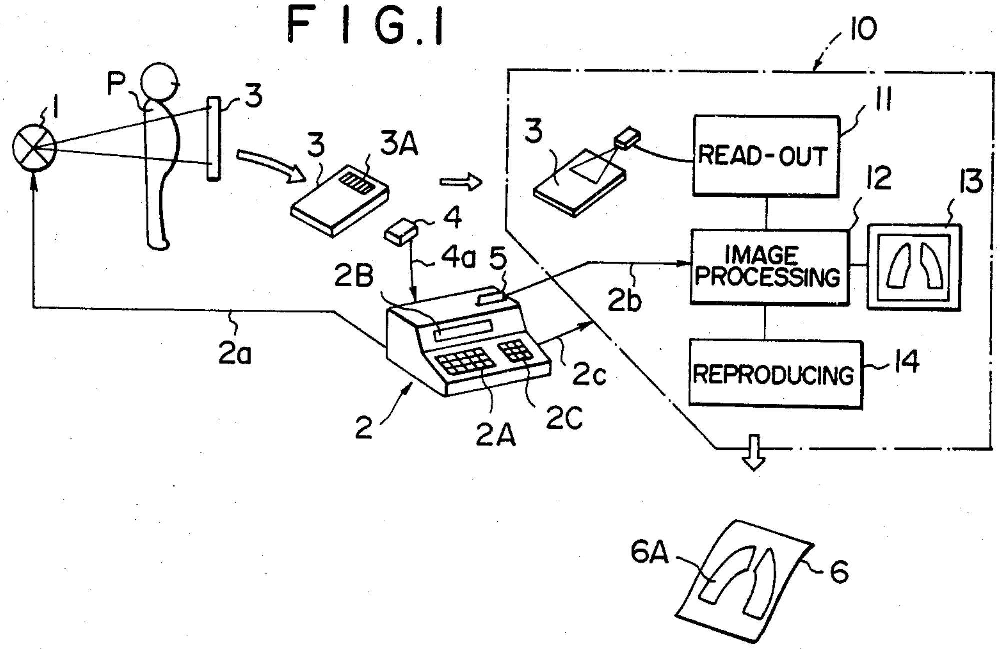
FIG. 1 is a schematic view showing an embodiment of the radiation image recording and reproducing system in accordance with the present invention.

FIG. 1 shows the general arrangement of an embodiment of the radiation image recording and reproducing system in accordance with the present invention. In this embodiment, the object is a patient and an X-ray source is used as the radiation source.

An X-ray source 1 for emitting X-rays to a patient P is connected with a controller 2 for adjusting the radiation exposure conditions of the X-ray source 1, such as the tube voltage, the tube current, and the exposure time. The X-rays emitted from the X-ray source 1 pass through a predetermined portion of the patient P, and an image recording sheet 3 comprising a stimulable phosphor is exposed to the X-rays passing through the portion of the patient P to have an X-ray image of the portion stored therein. On the rear surface of the sheet 3 is provided in advance a bar code 3A (i.e. an identification code), which is read out by a bar code reader 4. Upon reading out the bar code 3A, the bar code reader 4 generates a read-out signal 4*a* and sends it to the controller 2. In the controller 2 is incorporated a patient ID card reader for reading out the patient ID information (i.e. the object information) when a patient ID card 5 carrying the patient ID information stored therein is inserted into the patient ID card reader. The signals obtained by the read-out of the bar code 3A and the patient ID card 5 are sent from the controller 2 to an image processing and reproducing section 10. (The bar code reader 4 and the patient ID card reader need not necessarily be connected with or incorporated in the controller 2. Thus the bar code reader 4 and the patient ID card reader may be installed separately from the controller 2 and connected with the image processing and reproducing section 10.)

The X-ray image stored in the image recording sheet 3 is then read out by a read-out section 22 of the image processing and reproducing section 10. Thereafter, an electric image signal obtained by the read-out is processed in an appropriate manner (under the image processing conditions adjusted by the controller 2). The image signal thus processed is used to reproduce a visible image on a monitor television 13 for monitoring the reproduced X-ray image. Also, the image signal processed as described above is sent to an image reproducing section 14 in which a visible image 6A is reproduced in a photographic film by use of the image signal to form an image sheet 6 for diagnosis. The visible image 6A ultimately obtained in this manner has a high image quality which could not been obtained by the conventional radiography, and includes abundant diagnostic information.

Details of the construction and functions of the image processing and reproducing section 10 are described in many patent specifications, for example in those mentioned above, and may be incorporated in the present invention.

Figure 2:
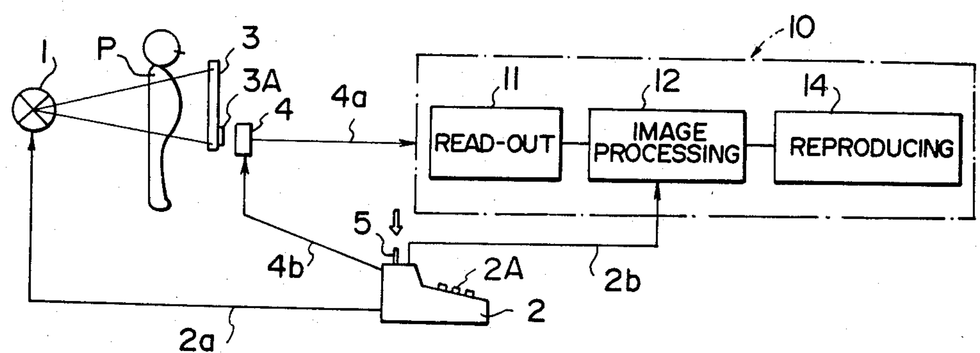
FIG. 2 is a schematic view showing another embodiment of the radiation image recording and reproducing system in accordance with the present invention.

In the image recording and reproducing system in accordance with the present invention as shown in FIG. 1 or 2, the controller 2 is provided with selection keys 2A for selecting the type of image recording and sending the signals specifying the radiation exposure conditions and the image processing conditions suitable for the type of image recording to the X-ray source 1 and the image processing section 12, thereby adjusting the radiation exposure conditions of the X-ray source 1 and the image processing conditions of the image processing section 12. When necessary ones of the selection keys 2A are pressed, an image recording condition setting signal 2*a* and an image processing condition setting signal 2*b* are generated according to the type of image recording thus selected, and respectively sent to the X-ray source 1 and the image processing section 12. In the case where a control section for activating the X-ray source 1 on the basis of the radiation exposure conditions of the X-ray source is built in the controller 2, the image recording condition setting signal 2*a* is not sent to the outside of the controller 2. Also, the signal 4*a* sent from the bar code reader 4 and the signal obtained by reading out the patient ID card 5 are fed as an ID signal 2*c* to the image processing and reproducing section 10. In the image processing and reproducing section 10 is incorporated a computer for carrying out necessary memorizing and processing operations upon receiving the signals 2*b* and 2*c*. In the electronic computer, the relationship between the image to be reproduced and the ID signal is clarified by known methods of information processing, and necessary image processing is carried out.

The controller 2 is also provided with a display section 2B for indicating the contents selected by the selection keys 2A on the keyboard. Further, input keys 2C such as numeric keys for manually inputting the ID contents are installed on the controller 2.

Figure 4:
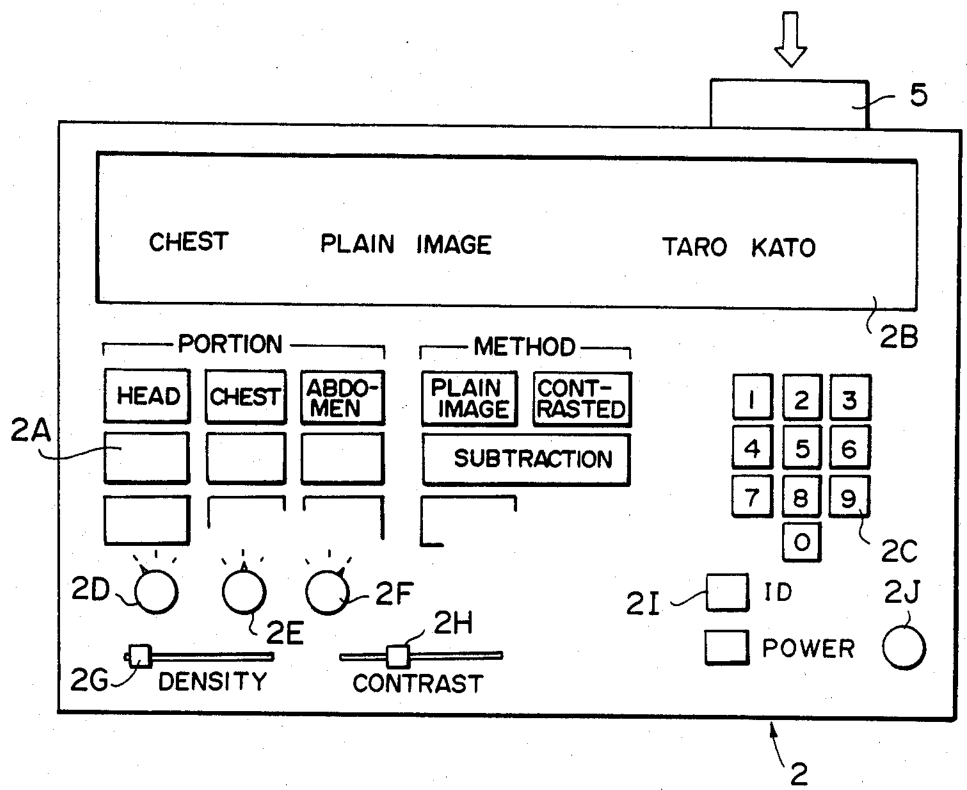
FIG. 4 is a front view showing an embodiment of the controller employed in the radiation image recording and reproducing system in accordance with the present invention.
Figure 5:
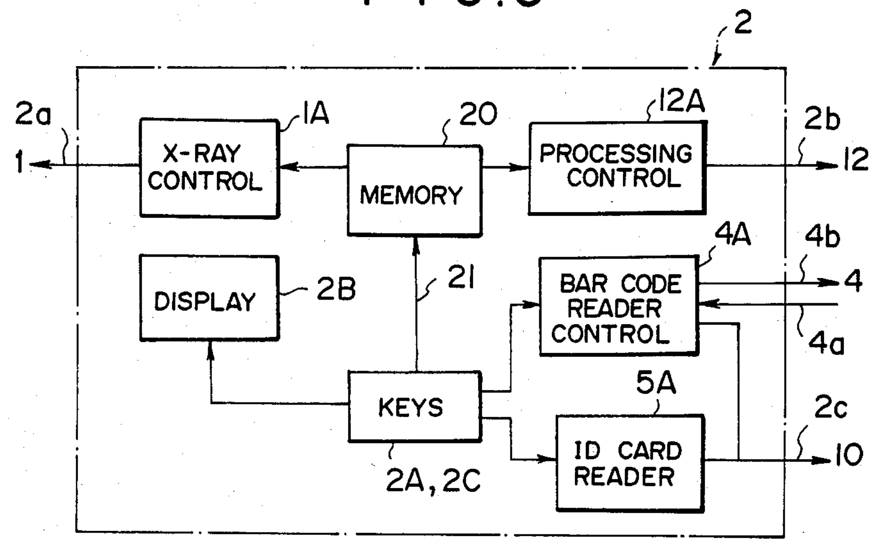
FIG. 5 is a block diagram showing an embodiment of the internal architecture of the controller employed in the radition image recording and reproducing system in accordance with the present invention.

FIGS. 4 and 5 show an embodiment of the architecture of the controller 2. In this embodiment, a card reader 5A for reading out the ID information from the patient ID card 5 inserted thereinto, and a bar code reader controller 4A for controlling the bar code reader 4 are incorporated in the controller 2. The controller 2 also has a setting condition memory 20 in which the image recording conditions and the image processing conditions are memorized in advance for each type of image recording. The setting condition memory 20 receives a signal 21 representing the type of image recording which is selected by the selection keys 2A on the keyboard, and outputs signals specifying setting conditions corresponding to the selected type of image recording via an X-ray controller 1A and an image processing controller 12A. The numeric keys 2C are positioned at a part of the keyboard so that the ID information and other necessaary information can be entered manually by use of the numeric keys 2C. On the keyboard are also positioned dials 2D, 2E and 2F for manually adjusting the tube voltage, the tube current and the exposure time of the X-ray source 1. The keyboard also has a density adjusting lever 2G and a contrast adjusting lever 2H for manually adjusting the image processing conditions, so that the image density and the image contrast can be manually adjusted to appropriate values. When an ID pushbutton 2I on the keyboard is depressed, the bar code reader controller 4A activates the bar code reader 4 to read out the bar code 3A of the image recording sheet 3. Alternatively, the bar code reader controller 4A may be activated by the insertion of the patient ID card 5 into the card reader 5A instead of by depressing the ID pushbutton 2I. In this case, the ID pushbutton 2I is used only when the patient ID information is manually entered by use of the numeric keys 2C. Namely, when the patient ID information is entered by use of the numeric keys 2C, the ID pushbutton 2I is first depressed, and then the numeric keys 2C are depressed. At this time, the bar code reader 4 is activated as the ID pushbutton 2I is depressed. Or, conversely, the numeric keys 2C may be depressed first, and then the ID pushbutton 2I may be depressed, thereby starting the input of the ID information and the read-out of the bar code reader 4.

The read-out signal 4*a* generated by the bar code reader 4 is returned to the bar code reader controller 4A, and sent to the image processing and reproducing setion 10 together with the output of the ID card reader 5A.

After the aforesaid conditions are adjusted according to the type of image recording selected by the selection keys 2A (or after the ID information is further inputted), an X-ray exposure button 2J is used to cause X-rays to emit from the X-ray source 1. The X-ray exposure button 2J may be utilized also for inputting of the aforesaid image processing conditions (i.e. the action for inputting the set information into the image processing section 12), or for inputting of the ID information and the bar code information read out by the bar code reader 4 (i.e. the action for sending the inputted value and the read-out value to the image processing and reproducing section 10). In this case, by depressing after the X-ray exposure button 2J after the adjustments of all (or some) conditions or the read-out is over, the signals 2*a*, 2*b* and 2*c* are transmitted and, at the same time, the X-ray source 1 is activated to emit X-rays.

In the embodiment of FIGS. 1, 4 and 5, the bar code reader 4 is connected only with the controller 2. However, it is also possible to construct the system so that the bar code reader 4 receives a start signal 4*a* from the controller 2, and the output signal 4*a* of the bar code reader 4 is directly sent to the image processing and reproducing section 10 without passing though the controller 2. FIG. 2 shows another embodiment of the radiation image recording and reproducing system in accordance with the present invention, which is constructed in the manner just described above.

In FIG. 2, similar elements are numbered with the same reference numerals and characters with respect to FIG. 1. In this embodiment, the bar code reader 4 is positioned at the rear of the image recording sheet 3 positioned for image recording in the system, so that the bar code 3A can be read while the image recording sheet 3 is positioned for image recording. The output signal 4*a* of the bar code reader 4 is directly sent to the image processing and reproducing section 10.

The above-described embodiments of the radiation image recording and reproducing system in accordance with the present invention are operated in the manner as described below. When an image of the patient P is recorded, the patient ID card 5 is received from the patient P and inserted into the card inlet of the controller 2. When the patient P comes to the image recording position at the image recording stand, a cassette containing a single image recording sheet 3 or a magazine containing many image recording sheets 3 is loaded into the predetermined position. At this time, the ID pushbutton 2I on the keyboard of the controller 2 is depressed to activate the bar code reader 4. Thus the read-out of the ID card 5 is carried out as the ID pushbutton 2I is depressed. Thereafter, the image recording portion of the patient P and the method of image recording (e.g. the frontal chest and the plain image recording method) are selected by use of the selection keys 2A on the keyboard. As a result, the signal 21 representing the selected type of image recording is entered into the setting condition memory 20, and the setting conditions corresponding to the selected type of image recording are selected from the data memorized in the memory 20 and sent to the X-ray controller 1A and the image processing controller 12A. When the exposure button 2J is depressed, the X-ray controller 1A controls the X-ray source 1 on the basis of the setting conditions so as to emit X-rays of a suitable dose from the X-ray source 1. On the other hand, the image processing controller 12A sends the image processing setting conditions suitable for the selected type of image recording to the image processing section 12 of the image processing and reproducing section 10, thereby adjusting the image processing conditions to desirable values. Also, the bar code information read out by the bar code reader 4 and the patient ID information read out by the ID card reader 5A are entered into and memorized in the computer of the image processing and reproducing section 10. After the image recording is completed, the X-ray image stored in the image recording sheet 3 is read out by the read-out section 11. Specifically, the sheet 3 is two-dimensionally scanned with stimulating rays such as a laser beam, and light emitted from the sheet 3 in proportion to the X-ray energy stored when the sheet 3 is exposed to the stimulating rays is photoelectrically detected and converted into an electric image signal. The electric image signal thus obtained is sent to the image processing section 12 and processed therein on the basis of the processing conditions specified by the image processing condition setting signal 2*b* and with reference to the signal 2*c* generated by the bar code reader 4. The image signal thus processed is displayed on the monitor television 13, so that the operator can monitor the image reproduced. The processed image signal is also sent to the image reproducing section 14 and used therein to reproduce the visible image 6A by point-by-point scanning on the image sheet 6 for diagnosis. At this time, the aforesaid patient ID information is also reproduced in the image sheet 6.

As described above, the X-ray image of the patient P is recorded under predetermined appropriate image recording conditions, processed under predetermined appropriate image processing conditions, and reproduced in the image sheet 6 for diagnosis together with the necessary ID information.

As mentioned above, in the radiation image recording and reproducing system in accordance with the present invention, since the image recording conditions and the image processing conditions are simultaneously adjusted by a single simple operation of selecting the type of image recording, no operation error arises, and a high efficiency is realized.

In the embodiments described above, the bar code reader 4 is activated by depressing the ID pushbutton 2I. However, it is also possible to use the ID pushbutton 2I as a control start button which is depressed after the selection keys 2A are depressed, thereby starting the input of the setting conditions and the operation of the bar code reader 4. Thus the activation of the bar code reader 4 can also be included in a single operation. For example, it is also possible to construct the system so that the meanings of the selection keys 2A are indicated on the display section 2B when the selection keys 2A are depressed, and then the ID pushbutton 2I used as the control start button is depressed after the contents indicated on the display section 2B are confirmed. When the ID pushbutton 2I is depressed, the condition setting signals 2*a* and 2*b* are entered respectively into the X-ray source 1 and the image processing section 12 and, at the same time, the bar code reader 4 is activated to read out the bar code 3A. In addition, the ID card reader 5A may also be activated to start reading out as the ID pushbutton 2I used as the control start button is depressed. In this case, the exposure button 2J is used only for starting the exposure to X-rays.

In the above-described embodiments, the activation of the bar code reader 4 and the read-out of the ID card 5 are conducted prior to the image recording. However, this sequence may be reversed. Namely, it is also possible to construct the system so that the ID pushbutton 2I is depressed after the selection keys 2A are depressed.

Figure 3:
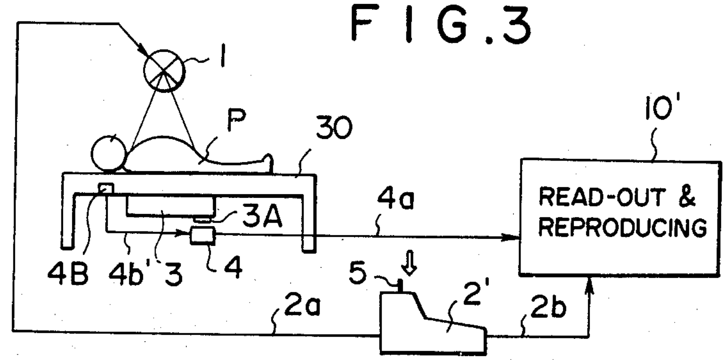
FIG. 3 is a schematic view showing a further embodiment of the radiation image recording and reproducing system in accordance with the present invention.

Further, in the aforesaid embodiments, the bar code reader 4 is connected with the controller 2. However, the bar code reader 4 need not necessarily be connected to the controller 2. For example, as shown in FIG. 3, the bar code reader 4 may be positioned in the vicinity of the bar code 3A, and a sensor 4B may be installed on an image recording table 30 on which the patient P lies. In this embodiment, the sensor 4B detects the presence of the patient P on the image recording table 30 and sends a detection signal 4*b*′ to the bar code reader 4. On the basis of the detection signal 4*b*′, the bar code reader 4 starts reading out the bar code 3A. In this case, it is advantageous for a function for detecting the loaded image recording sheet 3 to be provided and for the bar code reader 4 to be activated on the basis of the AND operation between the image recording sheet detection signal and the patient detection signal 4*b*′. Also in FIG. 3, similar elements are numbered with the same reference numerals and characters with respect to FIGS. 1 and 2.

Figure 6:
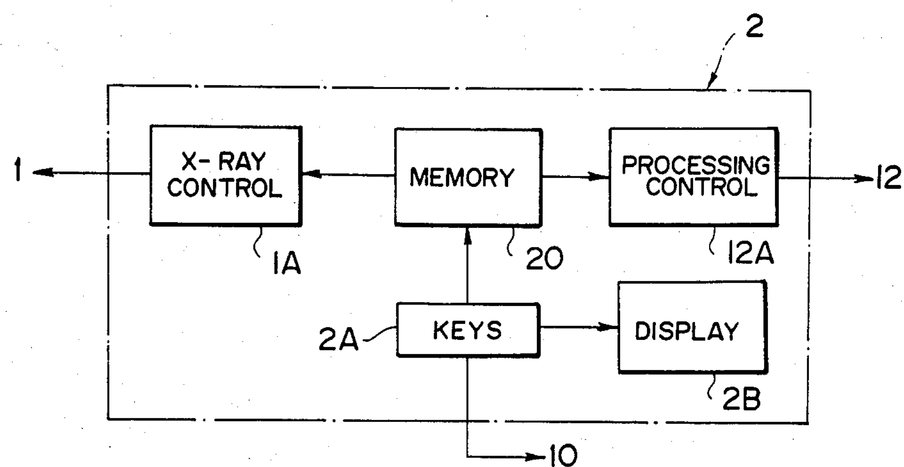
FIG. 6 is a block diagram showing a modified form of the internal architecture of the controller employed in the radiation image recording and reproducing system in accordance with the present invention.

In the embodiments described above, the ID card reader 5A is incorporated in the controller 2. However, instead of using the ID card reader 5A, it is also possible to input the ID information from the keyboard. Accordingly, it is possible to simplify the composition of the controller 2 as shown in FIG. 6. In this embodiment, the controller 2 comprises the keyboard provided with the keys having many functions, the setting condition memory 20, the X-ray controller 1A, the image processing controller 12A, and the display section 2B.

Also, in the aforesaid embodiments, the read-out of the ID information is started in response to the start of the read-out of the bar code reader 4, or the read-out of the ID information and the read-out of the bar code reader 4 are started simultaneously when the ID pushbutton 2I is depressed. However, this sequence may be reversed. That is, the bar code reader 4 may be started in response to the insertion of the ID card 5 into the ID card reader 5A.

As described above, in the present invention, the operation sequence is not limited to that described above, but may be modified in various manners.

I claim:

1. In a radiation image recording and reproducing system wherein a radiation is caused to pass through an object, said system including means for exposing a stimulable phosphor to said radiation passing through said object whereby a radiation image of said object is stored in said stimulable phosphor, means for exposing said stimulable phosphor to stimulating rays to photoelectrically read out said radiation image stored in said stimulable phosphor and obtain an electric image signal, means for subjecting said electric image signal to image processing according to the type of image reecording, and means for reproducing a visible image in accordance with said processed electric image signal, the improvement comprising: means for adjusting the conditions of exposure to said radiation and the processing conditions of said image processing, including means for selecting in a single action the setting conditions predetermined according to the type of image recording.

2. In a radiation image recording and reproducing system wherein a radiation is caused to pass through an object, said system including means for exposing a stimulable phosphor to said radiation passing through said object whereby a radiation image of said object is stored in said stimulable phosphor, said stimulable phosphor being provided with an identification code, means for reading out said identifiction code, memory means for storing said identification code and object information corresponding to said object wherein said stimulable phosphor is exposed to stimulating rays to read out said radiation image stored in said stimulable phosphor and obtain an electric image signal, said electric image signal is processed according to a type of image recording on the basis of at least one of said identification code and said object information memorized, and said processed electric image signal is reproduced into a visible image together with at least one of said identifiction code and said object information, the improvement comprising;

means for correctly correlating said identification code with said object information, including means for adjusting the conditions of exposure to said radiation and the processing conditions of said image processing by a first operator action of selecting according to the type of image recording from a plurality of predetermined setting conditions, and means for starting the read-out of said identification code and the exposure to said radiation by a second operator action.

3. A radiation image recording and reproducing system as defined in claim 2 wherein said first and second operator actions are carried out substantially simultaneously by a single operation.

4. A radiation image recording and reproducing system as defined in claim 2 wherein said means for reading out said identification code operates in response to said memory means.

5. A radiation image recording and reproducing system as defined in claim 2 wherein said memory means operates in response to said means for reading out said identification code.

6. In a radiation image recording and reproducing system wherein a radiation is caused to pass through an object, said system including means for exposing a stimulable phosphor to said radiation passing through said object whereby a radiation image of said object is stored in said stimulable phosphor, said stimulable phosphor being provided with an identification code, means for reading out said identification code, memory means for storing said identification code and object information corresponding to said object wherein said stimulable phosphor is exposed to stimulating rays to read out said radiation image stored in said stimulable phosphor and obtain an electric image signal, said electric image signal is processed according to a type of image recording on the basis of at least one of said identification code and said object information memorized, and said processed electric image signal is reproduced into a visible image together with at least one of said identification code and said object information, the improvement comprising: means for adjusting the conditions of exposure to said radiation and the processing conditions of said image processing by a single action of selecting the setting conditions predetermined according to the type of image recording, wherein said identifiction code reading out means is responsive to said identifiction code storing means.

* * * * *